United States Patent
Villar Gonzalez et al.

(10) Patent No.: US 6,494,915 B1
(45) Date of Patent: Dec. 17, 2002

(54) KNEE PROSTHESIS WITH MOBILE CONGRUENT INSERT

(75) Inventors: José Luis Villar Gonzalez, Paterna (ES); Javier De Gracia Castillo De Olivares, Paterna (ES)

(73) Assignee: Industrias Quirurgicas De Levante S.L., Paterna (ES)

( * ) Notice: Subject to any disclaimer, the term of this patent is extended or adjusted under 35 U.S.C. 154(b) by 0 days.

(21) Appl. No.: 09/600,570

(22) PCT Filed: Nov. 18, 1999

(86) PCT No.: PCT/ES99/00371

§ 371 (c)(1),
(2), (4) Date: Sep. 27, 2000

(87) PCT Pub. No.: WO00/30571

PCT Pub. Date: Jun. 2, 2000

(30) Foreign Application Priority Data

Nov. 19, 1998 (ES) ............................................. 9802429

(51) Int. Cl.[7] .................................................. A61F 2/38
(52) U.S. Cl. ................................. 623/20.33; 423/20.29
(58) Field of Search ........................... 623/20.28, 20.29, 623/20.3, 20.32, 20.33

(56) References Cited

U.S. PATENT DOCUMENTS 4,950,297 A * 8/1990 Elloy et al. .............. 623/20.29

FOREIGN PATENT DOCUMENTS

| EP | 0 177 755 | 4/1986 |
|---|---|---|
| EP | 0 749 734 A1 | 12/1996 |
| ES | 2 114 083 | 5/1998 |
| WO | WO 95/17860 | 7/1995 |
| WO | WO 97/30664 | 8/1997 |
| WO | WO 98/25550 | 6/1998 |

* cited by examiner

Primary Examiner—David J. Isabella
(74) Attorney, Agent, or Firm—Merchant & Gould P.C.

(57) ABSTRACT

Knee prosthesis with mobile congruent insert, presenting four well differenciated parts: a tibial part (1), a femoral, patellar part (2) and another part which replaces the meniscus of a human knee. The femoral and tibial parts are metal parts whereas the part which is called insert and substitutes the patella and the meniscus is made of plastic material more particularly polyethylene of ultra high molecular weight, and reproduces in its upper portion the geometry of the femoral condyles and in its lower planar portion has a bore (8) wherein is housed a pivot (4, 18) provided on the tibial tray (5, 19). The tibial part (1, 17) is comprised of a platen (5, 19) and an cross-shaped pin which prevents the rotation of the prosthesis once implanted.

5 Claims, 4 Drawing Sheets

KNEE PROSTHESIS WITH MOBILE CONGRUENT INSERT

BACKGROUND OF THE INVENTION

1. Field of the Invention

The knee joint prosthesis with mobile congruent insert subject of the present invention allows the pivoting rotation of the insert, this being inserted into a cylindrical tapping of the plastic piece.

The knee prosthesis is an implant destined to replace a deteriorated knee joint. The knee prosthesis (of the three-compartment type) is comprised of one femoral, one femoral, and one patellar component. The femoral component is made of metallic material and generally reproduces the condyles anatomic curvatures. The tibial component is generally comprised of a metallic tibial tray, a shaft and a spacer or an insert of plastic material (polyethylene) which forms the contact surface.

At the present, the main problem of this kind of prosthesis is that it gets loose, which requires its replacement with a new one by surgical operation.

Said loosening is due on one hand to the high stresses being transmitted in the interphase bone—implant, and on the other hand to the particles arising from the wear that causes the decay of the bone to which the prosthesis is attached.

The designs of knee prosthesis with mobile polyethylene insert therefore have the aim to reduce the forces in the interphase between the tibial component and the bone, and the decreasing of the polyethylene's wear by using contact surfaces with similar curvatures (congruencies) therefore achieving smaller contact pressures.

From the knee prostheses of this kind known in the art mention is to be made of those which have a tibial tray over which two plastic pieces drive independently, these plastic pieces generally sliding on curve-sided guides built in the tibial tray and being indicated for cases of conservation of the cruciate ligaments, or of the posterior cruciate ligament only.

The main inconvenience of prostheses having two independent mobile inserts is that they may turn up luxation problems as there exists the possibility that the plastic pieces might come out of the metallic or tibial piece, because they have no artificial bumpers to set up a limit to the movement, but they rather directly depend on the environment.

Another inconvenience of these prostheses is that the relative movement of some pieces with respect to the others is carried out by means of guides, the surgical technique therefore being very complicated, as any small failure which displaces any of the two parts of the guide causes coupling and performance problems during their work.

Another type of prostheses are those ones that have a rotating one-piece plastic insert, in case that both ligaments are sacrificed. The surfaces are completely congruent in extension in both configurations, there being a variant of this system, and being this one a prosthesis with a sliding plate, providing one grade more of liberty.

With this type of inserts there exist punctual contact areas between the insert and the rotation center or tray, said last point depending on the sliding system between the tray and the insert.

Another type of prosthesis exhibits a total congruence in extension by means of cylindrical surfaces, and the sliding of the insert with the platen is achieved by means of the conical elliptical shape of the base of the insert in a housing wrought in the tibial component, in such way that at the same time the insert rotates, the cone of the insert also rotates on its housing.

In these cases there also may appear zones of punctual contact between the cone of the insert and its metallic housing in the varus—valgus movements that are produced in the knee joint during the flexion—extension motion.

There also exists another knee prosthesis comprising a rotating one-piece insert of polyethylene showing a total congruence in extension and flexion, wherein the contact in extension is located in the zone of central support, while as the articulation is flexed, some lateral bands of the polyethylene insert with a radius similar to that of the femoral condyles in their posterior part come in contact.

These inserts with one sole pivotal center and total congruence in flexion and extension also require a very precise surgical technique, as they don't have any possibility of anterior posterior displacement.

SUMMARY OF THE INVENTION

All above mentioned inconveniences may be avoided by using the knee prosthesis with mobile congruent insert object of the present invention. In this prosthesis the surface of the plastic insert reproduces in its superior part of the geometry of the two femoral condyles, therewith, in comparison to other designs, the contact surface between both is largely increased (definition of the term congruence) what avoids punctual contact tensions that provoke the debilitation of the bone the prostheses are attached to, also lowering the effect of the existing shear stresses between the interphase insert—femoral component, avoiding the dislocation between both. In its completely planar lower part the insert has a tapping wherein is housed a pivot provided on the tibial tray.

On the contrary, the tibial part is composed of a platen and a keel-shaped shaft (cross-section) that avoids rotation of this component on the tibial axis once it has been implanted. In its superior part there is provided a cylindrical pivot located in the central middle third.

Over the surfaces of the plastic insert the surfaces of the condyles of the femoral component slide reproducing the flexion motion of a human knee. Also, the tapping allocated in the lower part of the insert fits into the cylindrical pivot of the tibial platen allowing a relative movement of the whole assembly, femoral component and insert, on the tibial component.

The advantages of the proposed invention are:

Congruence of the contact surfaces between the plastic component and the femoral component, total in extension and partial in flexion, leading this to a reduction of contact stresses and therefore of wear, this way lengthening the useful life of the implant and also considerably reducing its discomforts.

Light allowance of anterior—posterior movement thanks to the geometry existing between the femoral component and the plastic component and the rotary motion supported by the cylindrical tapping in the lower part of the insert through which the pivot of the metallic tray is introduced. Anterior—posterior displacement range that allows to correct light alignment failures of the articulation during the surgical operation, requiring a less rigorous technique and therefore facilitating the intervention, thereby implicating less risks for the patient.

This insert does not bear any guides that steer its relative movement with respect to the tibial tray, so, besides having a greater ability of movement And facilitating the surgical technique, this insert is freed from unnecessary and damaging stresses (sheer stresses and punctual tensions).

In order to facilitate a better comprehension of this disclosure and forming an integral part of it, shall be shown hereinafter a series of illustrating but not limiting drawings in which there is depicted the following:

DETAILED DESCRIPTION OF THE INVENTION

Figure 1:
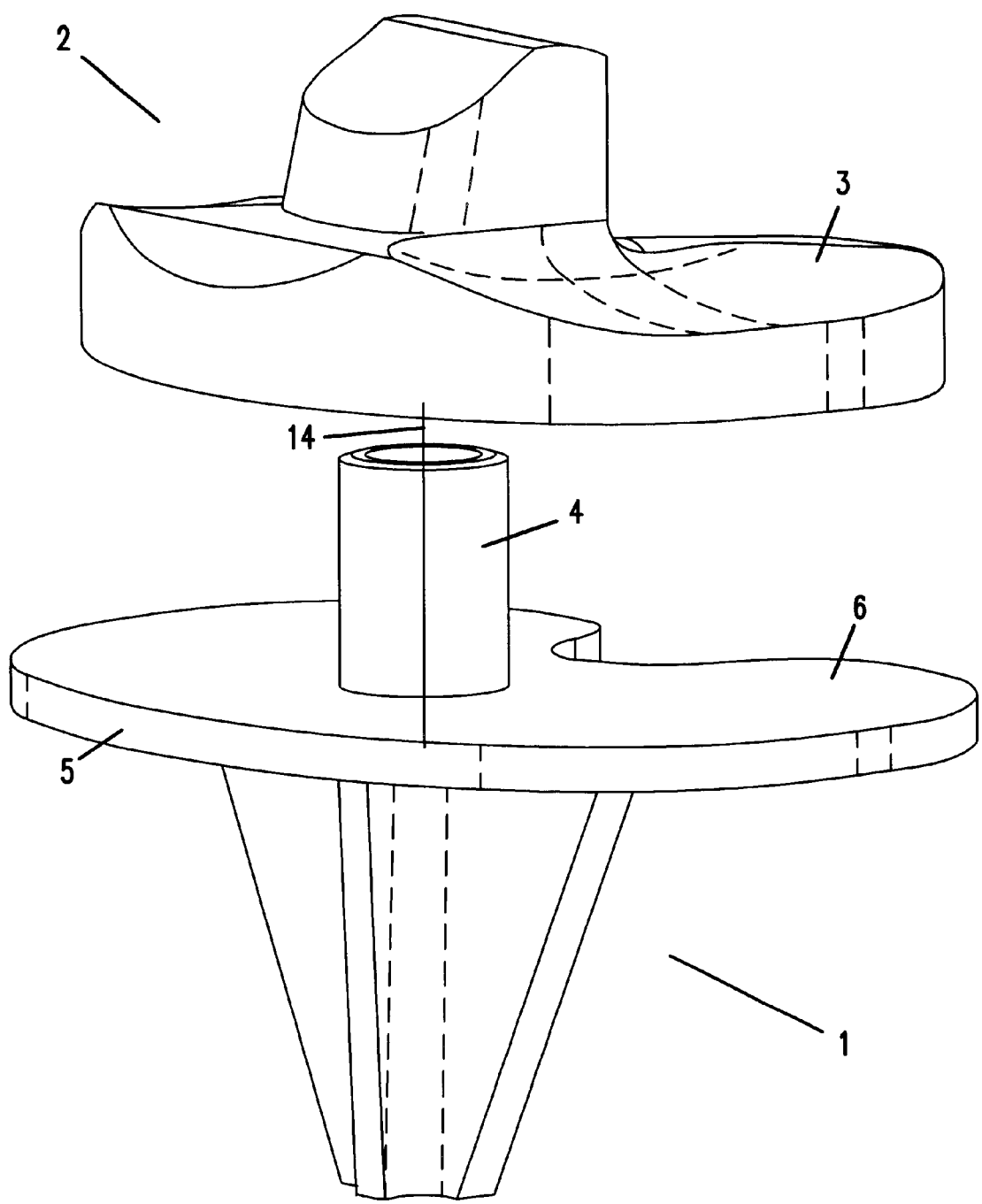
FIG. 1—Perspective view of the metallic and plastic parts of an embodiment of the prosthesis object of the present invention.
Figure 2:
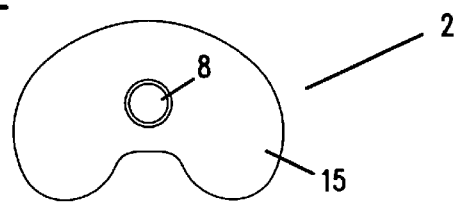
FIG. 2—Views of the plastic insert
Figure 2:
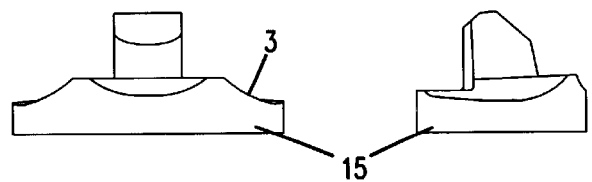
Figure 2:
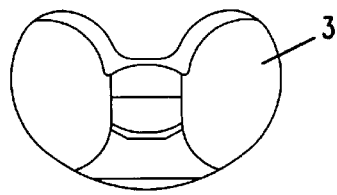
Figure 3:
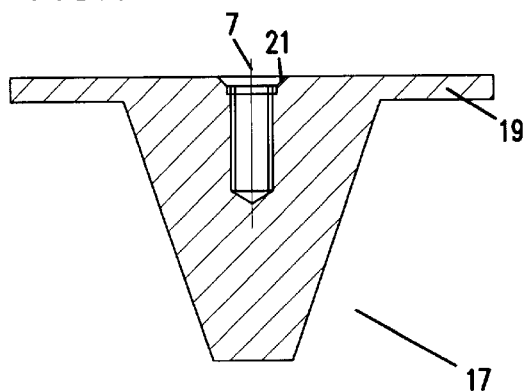
FIG. 3—Elevation and plan view of the metallic tray of a tibial component whose pivot is fixed into the metallic tray.
Figure 3:
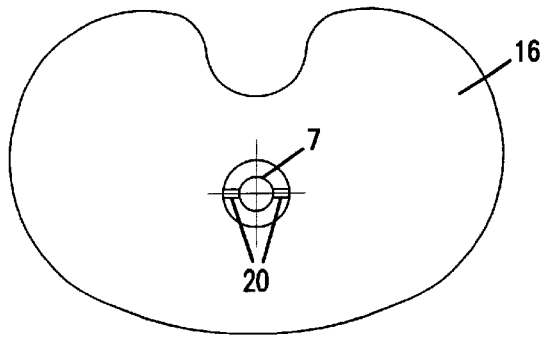
Figure 4:
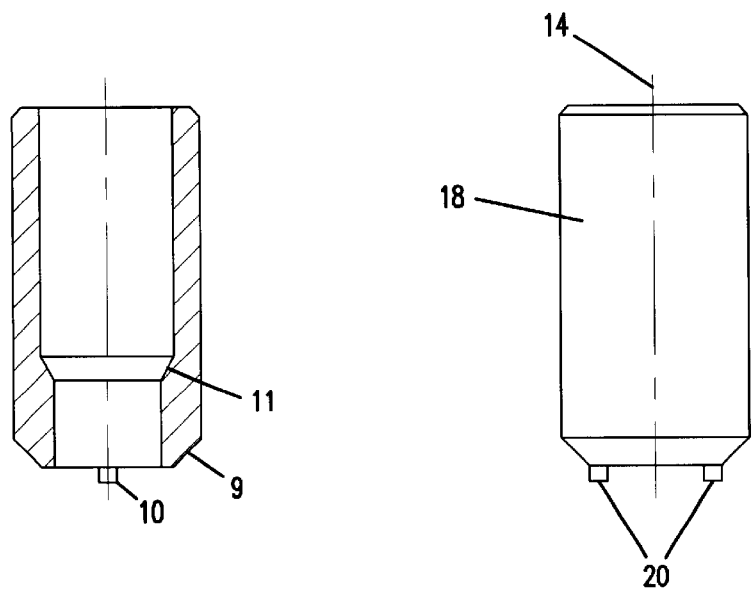
FIG. 4—Elevation and side view of the pin of a tibial component whose pivot is fixed into the metallic tray.
Figure 5:
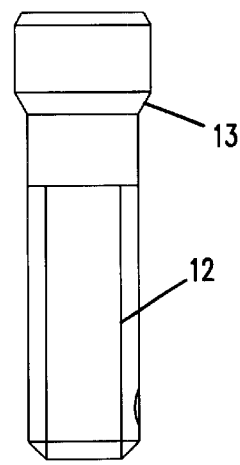
FIG. 5—Elevation and side views of the lockscrew of a tibial component whose pivot is fixed into the metallic tray.
Figure 5:
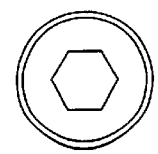
Figure 6:
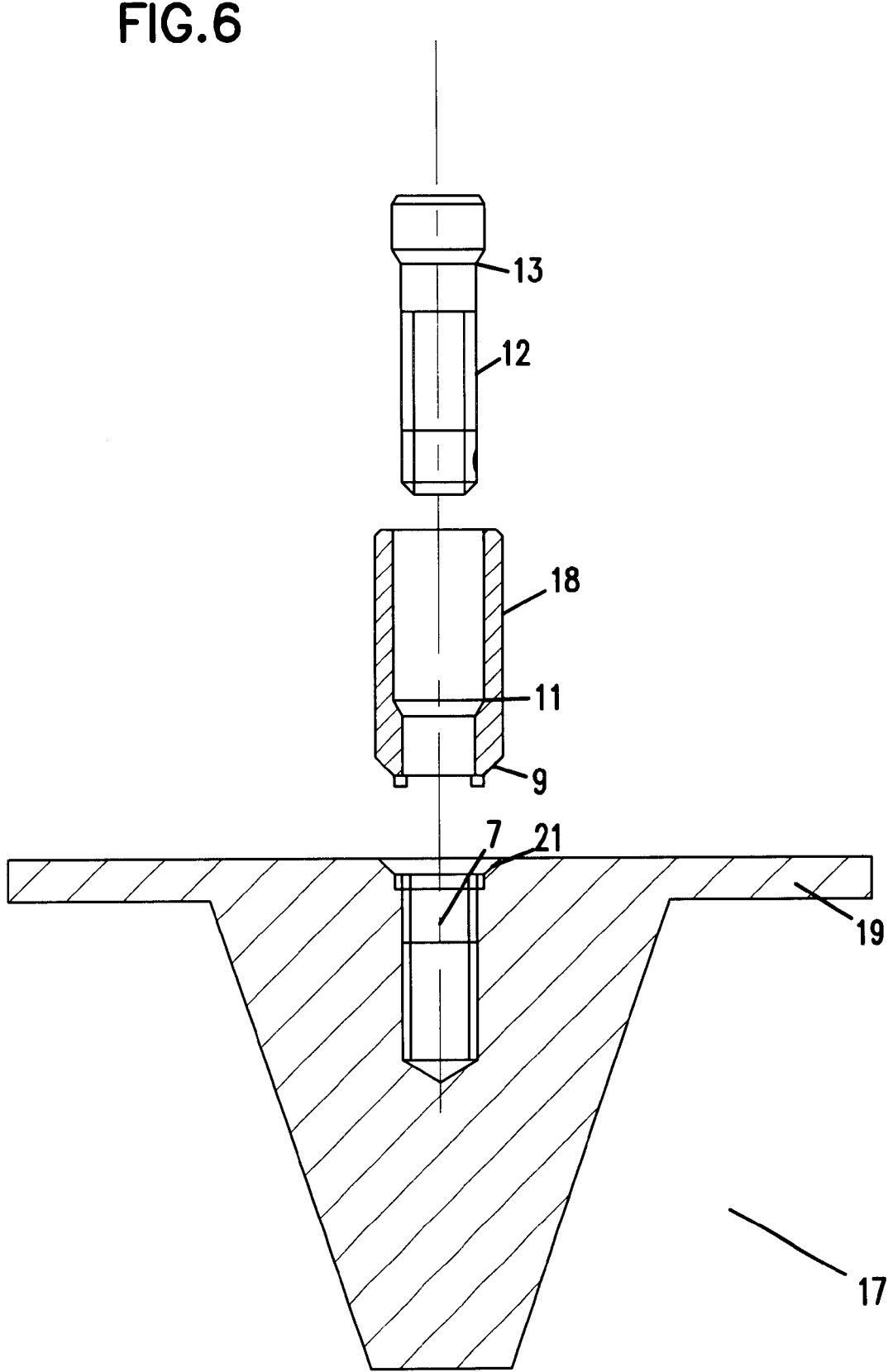
FIG. 6—Elevation and exploded view of the mounting assembly parts in a tibial component, whose pivot is fixed into the metallic tray.

As illustrated in the proposed FIGS. 1 and 2, there is a first assembly of the parts of a tibial component (1) with an insert (2) of one-piece polyethylene whose contact surface (3) reproduces the curvature of the femoral component at its lower area that lines up to the zone it is in contact with during the full extension of the articulation, allowing a certain medial-lateral displacement between both components, the lower surface (15) of the plastic component (2) being flat and smooth and sliding over the other flat and smooth surface (6) of the tray (5) of the tibial component (1).

The design of the present knee prosthesis involves a design of the insert (2) wherein there are provided condylar surfaces (3) with congruent radiuses to the condylar surface of the femur that determines, together with the pivot (4) of the tibial insert (1), the relative movement between the femoral component, the tibial insert (1) and the tray (5).

The polyethylene insert (2) slides at its lower surface by a rotary movement on the smooth surface (6) of a metallic tibial tray, this polyethylene insert being provided with a lower bore tapping (8) wherein there is lodged a pivot (4), joint to the metal tray (5), that limits the movement between the components, permitting free rotation.

It is this central pivot (4) together with the bore tapping (8) of the insert. (2) that renders possible the rotation of the plastic congruent insert on the tibial tray (5) and it can be joint to last one by means of two different systems:

One way would consist in the direct machining on the tibial tray, i.e., starting from an integrally cast part, whereby the pivot (4) and the tray (5) are the same piece as described above.

Another way is a system that includes:
a cylinder (18) with an adjusting arid self-centering warping cone (9), anti-rotation pins (10) and inner clamping cone (1).
a partially threaded screw provided of a clamping cone (13)
a tray (19) with anti-rotation slots (20), a threaded bore, an adjusting and self-centering warping cone (21)

While obtaining with both systems the same performance and application features, the difference is given by the means of joining the pin onto the tibial tray.

In this second system the pin (18) is allocated on the metallic tray (19), and that for the adjusting cone (21) of the tray (19) is adapted to match the adjusting cone (9) of the pin (18), the pivots (10) of the cylinder being adapted to match into the slots (20) of the tray (19). Next, the screw is introduced inside the cylinder (18) and this one is screwed to the tray (19) through its screwed bore (7). Thus, there exists a double Seat between the adjusting cones (21) of the tray and the cones (9) of the stem (18) and, the cones (13) of the lower part of the screw head and the inner cone (11) of the pin (18), thus avoiding rotation of the pivot and achieving a perpendicularity between the cone and the tray. So, there is achieved a perfect blocking that avoids the loosening of the system.

The present knee prosthesis allows rotary motion with respect to the axis (14) of the tibial tray (5) and anterior-posterior displacement of the femoral component upon the insert (2), in case that the pivot and the tibial tray should be one and the same piece. Also, in those cases where the mounting is the above explained, the axis (14) of the pivot (18) put on the tibial tray (19) will be the rotation axis.

This anterior-posterior movement occurs when the femoral component rotates upon itself, following this motion, sliding its congruent condylar surface on the congruent condylar surface (3) of the plastic part or insert (2) in such way that the stabilization rod (4, 18) of the insert joins the cam of the femoral component. As this shear force persists, both surfaces slide lightly lifting up in their posterior part, so describing said anterior-posterior movement.

To go back to the initial position, it is only needed to cease the stretch that produces this movement.

On the other hand, the rotation is free on the pivot (4, 18), that serves as rotation axis in this motion, having as limitations for this rotation only the proper limitations of human anatomy, and not being at no time an obstacle to the design of the present prosthesis.

At the same time, the link between the metallic tray (5, 19) and plastic (2) is the insertion of the pivot (4, 18) in its inferior housing (8) of the plastic component, without bumpers nor anchorages that limit its axial movement, therefore the same anatomic conditioners being those who limit such displacement, this movement not being affected by the properties of design or build-up of the different parts playing a role in this knee prosthesis.

Once the nature, as well as a practical application of the present invention, have been sufficiently depicted, we only have to add that form and materials of the invention are subject to modifications as long as they do not substantially affect the properties that shall be claimed as follows:

What is claimed is:

1. Knee prosthesis with mobile congruent insert capable of replacing a deteriorated knee articulation and allowing rotary movement with respect to one sole axis, comprising:
   a femoral component;
   a tibial component comprising a tibial insert and a tibial tray made of a metal and having a flat polished surface that bears a central pivot; and
   a patellar component;
   said knee prosthesis having a congruent one-piece plastic insert having a polished lower surface sliding, when in function, on the flat polished surface of the tibial tray in a way that a rotation axis of the plastic insert with respect to the tibial tray corresponds to an axis of the pivot, and having, at its lower surface, a cylindrical hole housing, when in function, the central pivot of the tibial component and allowing a free longitudinal movement of the pivot in said cylindrical hole;

said plastic insert furthermore having condylar surfaces with radii that generate surfaces congruent to a condylar surface of the femur which, combined with the central pivot of the tibial tray, determines the relative movement between the femoral component and the tibial component;

wherein the tibial component is made of an integrally cast one-piece element, the central pivot and the tibial tray being the same piece.

2. Knee prosthesis with mobile congruent insert capable of replacing a deteriorated knee articulation and allowing rotary movement with respect to one sole axis, comprising:

a femoral component;

a tibial component comprising a tibial insert and a tibial tray made of a metal and having a flat polished surface that bears a central pivot; and a patellar component;

said knee prosthesis having a congruent one-piece plastic insert having a polished lower surface sliding, when in function, on the flat polished surface of the tibial tray in a way that a rotation axis of the plastic insert with respect to the tibial tray corresponds to an axis of the pivot, and having, at its lower surface, a cylindrical hole housing, when in function, the central pivot of the tibial component and allowing a free longitudinal movement of the pivot in said cylindrical hole;

said plastic insert furthermore having condylar surfaces with radii that generate surfaces congruent to a condylar surface of the femur which, combined with the central pivot of the tibial tray, determines the relative movement between the femoral component and the tibial component;

wherein a fixation between the pivot and the tibial tray is achieved by means of the central pivot having an adjusting and self centering cone, anti-rotation pins and a lower adjusting cone provided to be engaged with a partially threaded screw with a head having a congruent cone. at its inferior part, and said tibial tray having anti-rotation slots, a threaded bore and an adjusting and self-centering cone provided to be engaged with the congruent cone of the central pivot.

3. The knee prosthesis according to claim 2, having a rotation-prevented and, with respect to the tibial tray, perpendicularly mounted central pivot by an adjustment of the cones of the tibial tray with the congruent cones of the central pivot, an adjustment of the anti-rotation pins with the slots of the tibial tray and an introduction of the partially threaded screw having a cone at the inferior part of its head through the interior of the central pivot into the threaded bore of the tibial component so as to allow an engagement of said cone to the lower adjusting cone within the central pivot.

4. The knee prosthesis according to claim 2, wherein the plastic insert is adapted to move longitudinally along the axis of the central pivot.

5. The knee prosthesis according to claim 2, wherein the femoral component further comprises a condylar surface, a congruent surface, a cam, and a posterior part, and an anterior-posterior motion occurs when the femoral component rotates around itself, the condylar and congruent surfaces of the femoral component sliding onto the condylar surfaces of the plastic insert in such a way that the central pivot acts as a bumper and as a guide onto the cam of the femoral component where, as long as this motion persists, both the condylar and congruent surfaces of the femoral component slide descending at the posterior part, thus performing said anterior-posterior movement similar to that of an anatomic knee.

* * * * *